United States Patent [19]
Shimamoto et al.

[11] Patent Number: 6,147,113
[45] Date of Patent: Nov. 14, 2000

[54] β-HYDROXYASPARTIC ACID DERIVATIVES

[75] Inventors: Keiko Shimamoto; Yoshimi Yasuda, both of Osaka; Masahiro Sakaitani, Kanagawa-ken; Bruno Lebrun, Osaka, all of Japan

[73] Assignee: Suntory Limited, Osaka, Japan

[21] Appl. No.: 08/957,440

[22] Filed: Oct. 24, 1997

[30] Foreign Application Priority Data

Oct. 25, 1996 [JP] Japan .................................. 8-318456

[51] Int. Cl.$^7$ .................................................. A61K 31/235
[52] U.S. Cl. .......................... 514/533; 514/547; 514/561; 514/567; 562/444; 562/568; 560/88; 560/196; 426/549; 426/611
[58] Field of Search .................................... 562/444, 568; 560/88, 196; 514/533, 547, 567, 561; 426/549, 611

[56] References Cited

U.S. PATENT DOCUMENTS 5,183,590   2/1993   Carter et al. .

FOREIGN PATENT DOCUMENTS

| 0 658 539 A1 | 6/1995 | European Pat. Off. . |
| 52-091822A | 8/1977 | Japan . |
| 07126250 | 5/1995 | Japan . |

OTHER PUBLICATIONS

Chem Abstracts 119:185900, Carter et al, RN=147696–99–9 1991.
Nicholls et al: "The release and uptake of excitatory amino acids", Tips Special Report, 1991, pp. 68–74.
Rothstein, et al: "Decreased Glutamate Transport by the Brain and Spinal Cord in Amyotrophic Lateral Sclerosis", The New England Journal of Medicine, May 28, 1992, vol. 326, No. 22, pp. 1464–1468.
Storck et al: "Structure, expression, and functional analysis of a Na+–dependent glutamate/aspartate transporter from rat brain", Proc.Natl.Acad.Sci.USA, vol. 89, pp 10955–10959, Nov. 1992, Neurobiology.
Arriza et al: "Functional Comparisons of Three Glutamate Transporter Subtypes Cloned from Human Motor Cortex", The Journal of Neuroscience, Sept. 1994, 14 (9), pp 5559–5569.
Fairman et al: "An Excitatory amino–acid transporter with properties of a ligand–gated chloride channel", Nature, vol. 375, Jun. 15, 1995, pp 599–603.
Arriza et al: "Excitatory amino acid transporter 5, a retinal glutamate transporter coupled a chloride conductance", Proc. Natl. Acad. Sci. USA, vol. 94, pp 4155–4160, Apr. 1997, Neurobiology.
Riordan et al: "Some Reactions of DL–trans–4, 5–Dicarbomethoxy–2–phenyl–2–oxazoline", J.Org.Chem., vol. 40, No. 22, 1975, pp. 3219–3221 Month Unavailable.
"Functional Comparisons of Three Glutamate Transporter Subtypes Cloned from Human Motor Cortex", Jeffrey L. Arriza, et al., The Journal of Neuroscience, Sept. 1994, pp. 5559–5569.
"New B–Hydroxyaspartate Derivatives Are Competitive Blockers for the Bovine Glutamate/Aspartate Transporter", Bruno Lebrun et al., The Journal of Biological Chemistry, vol. 22, No. 33, Aug. 15, 1997, pp. 20336–20339.
"Some Reactions of DL–trans–4.5–Dicarbomethoxy–2–phenyl–2–oxazoline", James M. Riordan, et al., J. Org. Chem., vol. 40, No. 22, 1975, pp. 3219–3221.

*Primary Examiner*—Samuel Barts
*Attorney, Agent, or Firm*—Pillsbury Madison & Sutro LLP

[57] ABSTRACT

The present invention provides blockers for glutamate transporters. During a series of syntheses searching for glutamate uptake inhibition in Xenopus oocytes injected with bovine glutamate transporter genes (BGLAST), we obtained β-hydroxyaspartic acid derivatives of the following chemical formula (1):

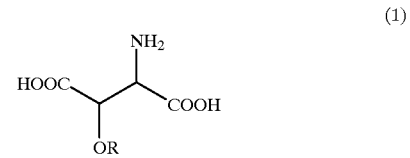

(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group; and salts thereof. These compounds are blockers of glutamate transporters, which are useful for the understanding of the function of glutamate transporters and show promise for the treatment of various neurodegenerative diseases.

12 Claims, No Drawings

β-HYDROXYASPARTIC ACID DERIVATIVES

BACKGROUND OF THE INVENTION

The present invention relates to L-glutamate uptake inhibitors, and more specifically β-hydroxyaspartic acid derivatives which have an inhibitory effect on the glutamate uptake activity of L-glutamate transporters.

The present compounds provide footholds for developing inhibitors of L-glutamate transporters to take up glutamate and for the treatment of neuropathies or neurodegenerative diseases such as epilepsy, Huntington's diseases, amyotrophic lateral sclerosis (ALS), and Alzheimer's diseases.

L-Glutamate has been known as an excitatory neurotransmitter in the mammalian central nervous system, which not only induces rapid neurotransmission between synapses but also participates in high-order and complex physiological processes such as memory or learning. Excitatory neurotransmission between synapses begins with release of glutamate from presynapses and terminates with rapid uptake of glutamate by high-affinity glutamate transporters present in presynapses and glial cells from synaptic clefts (Attwaell, D. and Nicholls, D., TIPS 68–74, 1991).

In certain genetic neurodegenerative diseases, a decrease of sodium-dependent glutamate uptake activity has been reported in the brains of some patients (Rothstein, J. D. et al., N. Eng. J. Med. 326, 1464–1468, 1992). This attracted the attention of researchers to the function of glutamate transporters in connection with these diseases, especially to the expression of the function and inhibition thereto.

Prior studies on glutamate transporters have concentrated on synaptosomes prepared from the brain or membrane samples prepared from kidney or small intestine. Approaches on the basis of molecular biology have also been made since 1992 when cDNAs of sodium-dependent high-affinity glutamate transporters were cloned (Pines, G. et al., Nature 360, 464–467, 1992; Storck, T. et al., Proc. Natl. Acad. Sci. USA, 89, 10955–10959, 1992; Kanai, Y. et al., Nature 360, 467–471, 1992). More recently, human glutamate transporter genes have been cloned and grouped into subtypes EAAT1 to 5 (Arriza, J. L. et al., J. Neurosci. 14, 5559–5569, 1994; Arriza, J. L. et al., Nature, 375, 599–603, 1995; Arriza, J. L. et al., Proc. Natl. Acad. Sci. 94, 4155 1997).

Up to the present, glutamate uptake inhibitors such as threo-β-hydroxyaspartate and CCG-III [(2S, 1'S, 2'R)-2-(2-carboxycyclopropyl)glycine] have been discovered as a result of the screening for glutamate uptake inhibitors by way of synaptosomes. These compounds are antagonists which by themselves are taken up as substrates by transporters, and hence, competitively inhibit glutamate uptake.

On the other hand, electrophysiological studies have shown that glutamate uptake inhibitors such as kainic acid and dihydrokainic acid act as a blocker rather than a competitive substrate because they inhibit glutamate uptake without being taken up by transporters. These compounds have also been shown to selectively act on EAAT2 (GLT-1 type) among the five EAAT subtypes (Arriza, J. L. et al., J. Neurosci. 14, 5559–5569, 1994). However, these compounds also act on ion channel-type glutamate receptors to induce a strong neuroexcitation.

Under these circumstances, there is a demand for the development of various inhibitors for glutamate transporters, especially those acting as a blocker, in order to elucidate relations between glutamate transporters and neuropathies or neurodegenerative diseases such as epilepsy, Huntington's diseases, amyotrophic lateral sclerosis (ALS), and Alzheimer's diseases.

SUMMARY OF THE INVENTION

The inventors have already developed a system for evaluating the inhibition of glutamate uptake by bovine or human glutamate transporters expressed on Xenopus oocytes from bovine or human glutamate transporter genes injected therein. Extensive study in search of glutamate uptake inhibitors using the system proved that novel β-hydroxyaspartic acid derivatives of the following chemical formula (1) inhibit glutamate uptake by these transporters and further that they do not induce a current but, in contrast, decrease the inward current induced by the uptake of glutamate into transporter-expressing oocytes. The present invention was accomplished based on these findings.

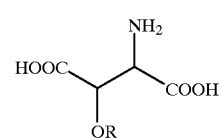

(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group. Accordingly, the present invention provides β-hydroxyaspartic acid derivatives of the chemical formula (1) and salts thereof as glutamate uptake blockers.

In the formula (1), the aromatic acyl group represented by R includes, for example, benzoyl, naphthoyl or a group wherein one or more hydrogen atoms on the ring may be substituted by a halogen atom, hydroxyl group, methoxy group or the like. The straight or branched lower aliphatic acyl group represented by R includes acetyl, propanoyl, n-butanoyl, sec-butanoyl, n-pentanoyl, sec-pentanoyl or the like.

In the formula (1), the aryl group represented by R includes phenyl, naphthyl or the like wherein one or more hydrogen atoms on the ring may be substituted by a halogen atom, hydroxyl group, methoxy group or the like. The aralkyl group represented by R includes benzyl, phenethyl or the like wherein one or more hydrogen atoms on the ring may be substituted by a halogen atom, hydroxyl group, methoxy group or the like. The straight or branched lower alkyl group represented by R includes methyl, ethyl, n-propyl, isopropyl, n-butyl, sec-butyl, tert-butyl or the like.

The compounds of the present invention can be converted into salts thereof by ordinary methods. These salts include alkali metal salts such as sodium salt and potassium salt; alkali earth metal salts such as calcium salt; ammonium salt; all of which are included in the present invention. All four isomers of each compound of the present invention, i.e. (2S, 3S), (2R, 3R), (2S, 3R) and (2R, 3S) isomers resulting from the presence of an asymmetric carbon atom at the 2- and 3-positions, are also included in the present invention.

Correlation between structure and activity of the compounds proved it important for the compounds of the present invention to have a bulky group as a substituent R and a relative configuration "threo" between the 2- and 3-positions in order to exhibit a strong activity. Any such bulky group as a desired substituent R can be introduced by a conventional technique according to the synthesis scheme shown below. Each of the four isomers can be synthesized from β-hydroxyaspartic acid having the corresponding configuration.

The compounds of the present invention can be synthesized as follows. For example, the compounds wherein R is an acyl group can be synthesized by protecting the amino group and the carboxyl group by an ordinary method, then converting the hydroxyl group to a desired acyloxy group, followed by deprotection according to the following scheme:

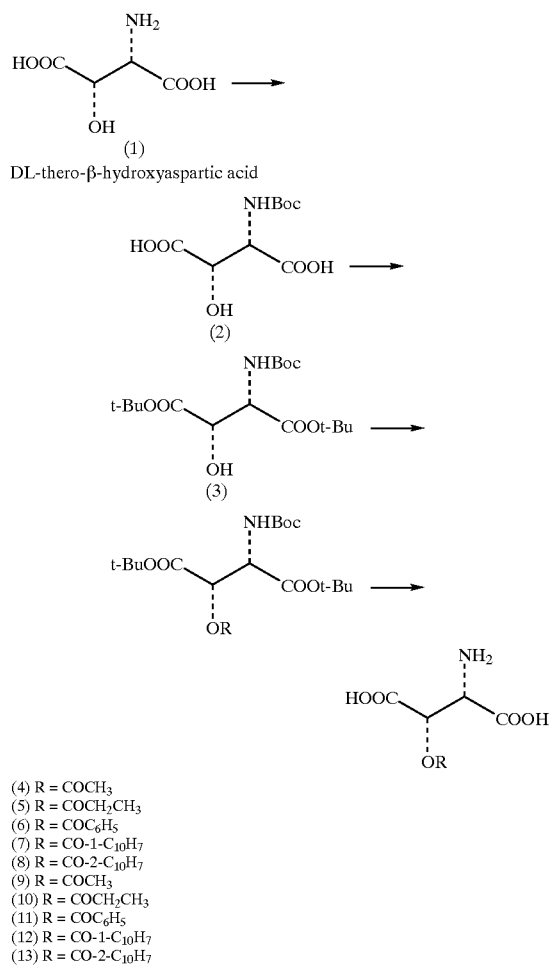

(4) R = COCH$_3$
(5) R = COCH$_2$CH$_3$
(6) R = COC$_6$H$_5$
(7) R = CO-1-C$_{10}$H$_7$
(8) R = CO-2-C$_{10}$H$_7$
(9) R = COCH$_3$
(10) R = COCH$_2$CH$_3$
(11) R = COC$_6$H$_5$
(12) R = CO-1-C$_{10}$H$_7$
(13) R = CO-2-C$_{10}$H$_7$ wherein Boc represents t-butoxycarbonyl group, t-Bu represents tert-butyl group and R represents a desired acyl group. According to the above scheme, the compounds bearing a desired acyl group as R can be obtained by reacting the compound (3) with acetic anhydride (when R is acetyl) or with an acyl chloride corresponding to the desired R. For example, (2S*, 3S*)-3-acetoxyaspartic acid (9) wherein R is acetyl is obtained by reacting the compound (3) with acetic anhydride, (2S*, 3S*)-3-propanoyloxyaspartic acid (10) wherein R is propanoyl is obtained by reacting the compound (3) with propionyl chloride, and (2S*, 3S*)-3-benzoyloxyaspartic acid (11) wherein R is benzoyl is obtained by reacting the compound (3) with benzoyl chloride. Here, (2S*, 3S*) means a mixture of threo-isomers having configurations (2S, 3S) and (2R, 3R).

The compounds of ether formed wherein R is an aryl, aralkyl or alkyl group can be synthesized by protecting the amino group and the carboxyl group by an ordinary method, then introducing a desired substituent in place of the hydroxyl group, followed by deprotection. For example, (2S*, 3S*)-3-benzyloxyaspartic acid (15) wherein R is benzyl can be synthesized starting from the previous synthesis intermediate (3) according to the following scheme:

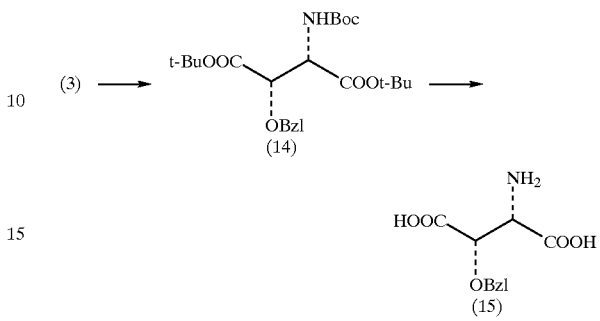

wherein Bzl represents benzyl, Boc represents t-butoxycarbonyl group and t-Bu represents tert-butyl. If benzyl bromide is replaced by a desired aryl, aralkyl or alkyl bromide in this scheme, a compound having the corresponding substituent R can be obtained.

The compounds of the present invention inhibit glutamate uptake into oocytes in a system of Xenopus oocytes expressing bovine BGLAST and human EAAT1 or EAAT2 from cRNAs introduced therein. In the same oocytes, the compounds of the present invention decrease the current induced by glutamate uptake rather than induce a current by themselves. This fact shows that the compounds act as a blocker. Thus, it is considered that the compounds of the present invention are useful for the understanding of the role of glutamate transporters in neurodegenerative diseases and that they are promising for the treatment of these neuropathies through investigation on correlation between structure and activity of drugs, etc.

The following examples illustrate the present invention without, however, limiting the same thereto.

EXAMPLES

Example 1

Synthesis of (2S*, 3S*)-3-Acetoxyaspartic Acid (9)

Step 1. Synthesis of di-t-butyl (2S*, 3S*)-N-t-butoxycarbonyl-3-hydroxyaspartate (3)

To 1.37 g (5.5 mmol) of a known compound (2S*, 3S*)-N-t-butoxycarbonyl-3-hydoxyaspartic acid (2) was added 10.5 ml (44 mmol) of N,N-dimethylformamide di-t-butylacetal at room temperature under nitrogen stream. Then, the mixture was warmed at 60° C. under stirring for two hours. The mixture was extracted with ether, and the organic layer was washed with water, then saturated brine and then dried over magnesium sulfate. The solvent was distilled off and the residue was purified by silica gel column chromatography (ethyl acetate/hexane=1/9). The resulted oily product was crystallized from hexane to give 1.68 g of the title compound (3) (yield 85%).

Properties: colorless prisms.

m.p.: 106–107° C.

$^1$H NMR (400 MHz, CDCl$_3$, δppm): 1.40 (s, 9H), 1.50 (s, 18H), 3.12 (d, 1H, J=5.0 Hz), 4.53 (dd, 1H, J=5.0, 2.0 Hz), 4.68 (d, 1H, J=10 Hz), 5.14 (d, 1H, J=10 Hz).

Step 2. Synthesis of di-t-butyl (2S*, 3S*)-3-acetoxy-N-t-butoxycarbonylaspartate (4)

To a solution of 500 mg (1.38 mmol) of the compound (3) obtained in Step 1 in pyridine (3 ml) was added 1 ml of acetic anhydride, and the mixture was stirred at room temperature for 20 hours. The mixture was extracted with ether, and the organic layer was washed with water, followed by saturated brine and then dried over magnesium sulfate. The solvent was distilled off and the residue was purified by silica gel column chromatography (ethyl acetate/hexane=1/9) to give 550 mg of the title compound (4) (yield 99%).

$^1$H NMR (400 MHz, CDCl$_3$, δppm): 1.40 (s, 9H), 1.43 (s, 9H), 1.50 (s, 9H), 2.13 (s, 3H), 4.90 (brd, 1H, J=10 Hz), 5.18 (brd, 1H, J=10 Hz), 5.50 (brs, 1H).

Step 3. Synthesis of (2S*, 3S*)-3-acetoxyaspartic acid (9)

To a solution of 202 mg (0.50 mmol) of the compound (4) obtained in Step 2 in chloroform (2 ml) was added 2 ml of trifluoroacetic acid, and the mixture was stirred at room temperature for 20 hours. The solvent was distilled off and the residue was purified by C18 silica gel column chromatography (RP-C18, distilled water) to give 43 mg of the title compound (9) (yield 45%).

$^1$H NMR (400 MHz, D$_2$O, δppm): 2.05 (s, 3H), 4.19 (d, 1H, J=2 Hz), 5.38 (d, 1H, J=2 Hz).

Example 2

Synthesis of (2S*, 3S*)-3-Propanoyloxyaspartic Acid (10)

Step 1. Synthesis of di-t-butyl (2S*, 3S*)-N-t-butoxycarbonyl-3-propanoyloxyaspartate (5)

To a solution of 300 mg (0.83 mmol) of the compound (3) in CH$_2$Cl$_2$ (6 ml) were added 0.5 ml of triethylamine and 0.3 ml of propionyl chloride, and the mixture was stirred at room temperature for 2 hours. The mixture was extracted with ether, and the organic layer was washed with water, followed by saturated brine and then dried over magnesium sulfate. The solvent was distilled off and the residue was purified by silica gel column chromatography (ethyl acetate/hexane=1/9) to give 303 mg of the title compound (5) (yield 87%).

$^1$H NMR (400 MHz, CDCl$_3$, δppm): 1.12 (t, 3H, J=7.0 Hz), 1.40 (s, 9H), 1.42 (s, 9H), 1.50 (s, 9H), 2.40 (m, 2H), 4.88 (brd, 1H, J=11 Hz), 5.15 (brd, 1H, J=11 Hz), 5.48 (brs, 1H).

Step 2. Synthesis of (2S*, 3S*)-3-propanoyloxyaspartic acid (10)

The procedure of Step 3 of Example 1 was repeated starting from 195 mg (0.47 mmol) of the compound (5) to give 92.5 mg of the title compound (10) (yield 96%).

$^1$H NMR (400 MHz, CD$_3$OD, δppm): 1.12 (t, 3H, J=7 Hz), 2.45 (q, 2H, J=7 Hz), 4.53 (d, 1H, J=2 Hz), 5.72 (d, 1H, J=2 Hz).

Example 3

Synthesis of (2S*, 3S*)-3-Benzoyloxyaspartic Acid (11)

Step 1. Synthesis of di-t-butyl (2S*, 3S*)-3-benzoyloxy-N-t-butoxycarbonylaspartate (6)

The procedure of Step 1 of Example 2 was repeated starting from 300 mg (0.83 mmol) of the compound (3) and replacing propionyl chloride by benzoyl chloride to give 291 mg of the propinyl chloride (6) (yield 75%).

$^1$H NMR (400 MHz, CDCl$_3$, δppm): 1.30 (s, 9H), 1.40 (s, 9H), 1.43 (s, 9H), 4.95 (brd, 1H, J=10 Hz), 5.23 (brd, 1H, J=10 Hz), 5.60 (d, 1H, J=4 Hz), 7.35 (t, 2H, J=6 Hz), 7.50 (t, 1H, J=8 Hz), 7.92 (d, 2H, J=8 Hz).

Step 2. Synthesis of (2S*, 3S*)-3-benzoyloxyaspartic acid (11)

The procedure of Step 3 of Example 1 was repeated starting from 152 mg (0.33 mmol) of the compound (6) to give 66 mg of the title compound (11) (yield 80%).

$^1$H NMR (400 MHz, DMSO-d6, δppm): 4.20 (d, 1H, J=10 Hz), 5.36 (d, 1H, J=10 Hz), 7.50 (t, 2H, J=8 Hz), 7.68 (t, 1H, J=8 Hz), 8.15 (d, 2H, J=8 Hz).

(DMSO-d6 represents dimethyl sulfoxide wherein all the hydrogens are deuterated.)

Example 4

Synthesis of (2S*, 3S*)-3-(1-Naphthoyl) Oxyaspartic Acid (12)

The procedure of Step 1 of Example 2 was repeated starting from 100 mg (0.27 mmol) of the compound (3) and replacing propionyl chloride by 1-naphthoyl chloride to give di-t-butyl (propinyl chloride)-N-t-butoxycarbonyloxy- 3-(1-naphthoyl)aspartate (7), which was treated in the same manner as in Step 3 of Example 1 without purification to give 82.5 mg of the title compound (12) (yield in two steps 70%).

$^1$H NMR (400 MHz, DMSO-d6, δppm): 4.23 (d, 1H, J=12 Hz), 5.50 (d, 1H, J=12 Hz), 7.63 (m, 3H), 8.03 (d, 1H, J=9 Hz), 8.20 (d, 1H, J=9 Hz), 8.40 (d, 1H, J=9 Hz), 8.80 (d, 1H, J=9 Hz).

Example 5

Synthesis of (2S*, 3S*)-3-(2-Naphthoyl) Oxyaspartic Acid (13)

Step 1. Synthesis of di-t-butyl (2S*, 3S*)-N-t-butoxycarbonyl-3-(2-naphthoyl)oxyaspartate (8)

The procedure of Step 1 of Example 2 was repeated starting from 300 mg (0.83 mmol) of the compound (3) and replacing propionyl chloride by 2-naphthoyl chloride to give 95.5 mg of the title compound (8) (yield 22%).

$^1$H NMR (400 MHz, CDCl$_3$, δppm): 1.35 (s, 9H), 1.42 (s, 9H), 1.48 (s, 9H), 5.05 (brd, 1H, J=10 Hz), 5.37 (brd, 1H, J=10 Hz), 5.72 (s, 1H), 7.55 (m, 2H), 7.83 (s, 2H, J=10 Hz), 7.95 (d, 1H, J=10 Hz), 8.00 (d, 1H, J=lOHz), 8.60 (s, 1H).

Step 2. Synthesis of (2S*, 3S*)-3-(2-naphthoyl)oxyaspartic acid (13)

The procedure of Step 3 of Example 1 was repeated starting from 82 mg (0.16 mmol) of the compound (8) to give 46 mg of the title compound (13) (yield 95%).

$^1$H NMR (400 MHz, DMSO-d6, δppm): 4.25 (d, 1H, J=10 Hz), 5.43 (d, 1H, J=10 Hz), 7.63 (m, 2H), 8.05 (m, 4H), 8.83 (s, 1H).

Example 6

Synthesis of (2S*, 3S*)-3-Benzyloxyaspartic Acid (15)

Step 1. Synthesis of di-t-butyl (2S*, 3S*)-3-benzyloxy-N-t-butoxycarbonylaspartate (14)

To a solution of 78 mg (0.22 mmol) of the compound (3) in DMF (3 ml) were added 13 mg (0.32 mmol) of sodium hydride and 16 mg (0.04 mmol) of tetra-n-butylammonium iodide at −20° C., and the mixture was stirred for 10 minutes, then 38 μl (0.32 mmol) of benzyl bromide was added and the mixture was stirred at 0° C. for one hour. The mixture was extracted with ether and the organic layer was washed with water, followed by saturated brine and then dried over magnesium sulfate. The solvent was distilled off and the residue was purified by silica gel column chromatography (ether/hexane=1/9) to give 65 mg of the title compound (14) (yield 65%).

$^1$H NMR (400 MHz, CDCl$_3$, δppm): 1.40 (s, 18H), 1.50 (s, 9H), 4.40 (d, 1H, J=11 Hz), 4.42 (d, 1H, J=3 Hz), 4.73 (dd, 1H, J=3, 10.5 Hz), 4.80 (d, 1H, J=11 Hz), 5.26 (d, 1H, J=10.5 Hz), 7.32 (m, 5H).

Step 2. Synthesis of (2S*, 3S*)-3-benzyloxyaspartic acid (15)

To a solution of 65 mg (0.14 mmol) of the compound (14) in chloroform (2 ml) was added 2 ml of trifluoroacetic acid, and then the mixture was stirred at room temperature for 20 hours. The solvent was distilled off and the residue was subjected to column chromatography on ion exchange resin (Dowex 50Wx4) and washed with water, then eluted with 1N aqueous ammonia to give 23 mg of the title compound (15) (yield 65%).

$^1$H NMR (400 MHz, DMSO-d6, δppm): 4.01 (d, 1H, J=2.5 Hz), 4.34 (d, 1H, J=2.5 Hz), 4.44 (d, 1H, J=11.5 Hz), 4.73 (d, 1H, J=11.5 Hz), 7.42 (m, 5H).

Evaluation Example 1

Determination of glutamate uptake inhibition in Xenopus oocytes injected with bovine glutamate transporter gene (BGLAST)

According to the protocol of our prior patent pplication (see Japanese Patent Public Disclosure No. 126250/95), Xenopus oocytes expressing bovine glutamate transporter gene BGLAST were obtained. Glutamate uptake activity was measured by liquid scintillation counting of radioactivity which completely lysed oocytes so that it was taken up by them after they were incubated with 1 μM L-[$^{14}$C] glutamate (11 GBq/mmol) and each sample at 100 μM for 20 minutes.

The compounds of the present invention showed glutamate uptake inhibitory activity, e.g. (2S*, 3S*)-3-benzoyloxyaspartic acid (11), (2S*, 3S*)-3-(1-naphthoyl) oxyaspartic acid (12) and (2S*, 3S*)-3-(2-naphthoyl) oxyaspartic acid (13) showed glutamate uptake inhibitory activities of 79%, 63% and 63%, respectively.

Evaluation Example 2

Determination of glutamate uptake inhibition in Xenopus oocytes injected with human glutamate transporter gene (EAAT1 or 2)

Glutamate uptake activity of (2S*, 3S*)-3-benzyloxyaspartic acid (15) was measured in the same manner as in Evaluation Example 1 using oocytes expressing cRNA of human EAAT1 or EAAT2 prepared by the previous protocol. The compound (15) showed inhibition of 74% for EAAT1 and 99% for EAAT2 at the concentration of 100 μM.

Evaluation Example 3

Electrophysiological evaluation in Xenopus oocytes injected with bovine glutamate transporter gene (BGLAST)

In oocytes expressing cRNA of bovine BGLAST prepared by the previous protocol, 100 μM glutamate induced an inward current of about 125 nA. However, the compounds of the present invention (2S*, 3S*)-3-benzoyloxyaspartic acid (11), (2S*, 3S*)-3-(1-naphthoyl)oxyaspartic acid (12) and (2S*, 3S*)-3-(2-naphthoyl)oxyaspartic acid (13) did not induce any inward current at the concentration of 100 μM. When 100 μM glutamate and each of these compounds at 100 μM were simultaneously added, the inward current induced by glutamate uptake was remarkably reduced. The rates of inhibition by the compounds (11), (12) and (13) were 50%, 40% and 20%, respectively.

These results prove that the compounds of the present invention are useful as inhibitors of glutamate transporter.

The present invention provides β-hydroxyaspartic acid derivatives and salts thereof which are inhibitors of glutamate transporter. The novel compounds inhibit glutamate uptake activity, and they are not only useful biochemical reagents for the understanding of the function of glutamate transporters but also promising tools for developing treatment methods of various neurodegenerative diseases through such studies.

What is claimed is:

1. A β-hydroxyaspartic acid derivative of the following chemical formula (1):

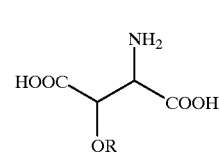

(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group, provided that R cannot be benzoyl; and a salt thereof.

2. The compound according to claim 1 as a threo-β-hydroxyaspartic acid derivative wherein the relative configuration of the 2- and 3-positions is threo; and a salt thereof.

3. A method of inhibiting the uptake of glutamate by cells expressing a L-glutamate transporter, comprising administering a β-hydroxyaspartic acid derivative to cells expressing a L-glutamate transporter, in an amount sufficient to inhibit the uptake of glutamate, said β-hydroxyaspartic acid derivative having the following chemical formula (1):

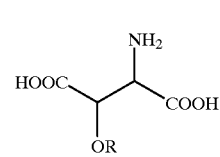

(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group; or a salt thereof.

4. A method of treating a patient having neuropathy or a neurodegenerative disease wherein a L-glutamate transporter is involved in the onset or development of the disease, comprising administering a β-hydroxyaspartic acid derivative in a pharmaceutically effective amount, to a patient in need of treatment for a neuropathy or a neurodegenerative disease, said β-hydroxyaspartic acid derivative having the following chemical formula (1):

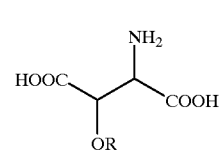

(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group; or a salt thereof.

5. Method according to claim 4, wherein the neuropathy or neurodegenerative disease is selected from the group consisting of epilepsy, Huntington's diseases, amyotrophic lateral sclerosis (ALS), and Alzheimer's diseases.

6. A composition for inhibiting the uptake of glutamate into cells expressing a L-glutamate transporters thereon comprising a β-hydroxyaspartic acid derivative of the following chemical formula (1):

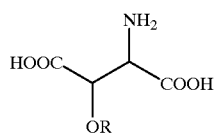
(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group; or a salt thereof, together with a carrier.

7. A pharmaceutical composition comprising as an active ingredient a β-hydroxyaspartic acid derivative of the following chemical formula (1):

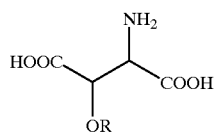
(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group; or a salt thereof, together with a pharmaceutically acceptable exciptient or carrier.

8. A pharmaceutical composition according to claim 7, for the treatment of a neuropathy or a neurodegenerative disease wherein a L-glutamate transporter activity is involved in the onset or development of the disease.

9. A pharmaceutical composition according to claim 8, wherein the neuropathy or neurodegenerative disease is selected from the group consisting of epilepsy, Huntington's diseases, amyotrophic lateral sclerosis (ALS), and Alzheimer's diseases.

10. A pharmaceutical composition according to claim 8, wherein 0.1–100 mg of the active ingredient is contained in a unit dose.

11. A pharmaceutical composition according to claim 8, which is an oral composition.

12. A food composition comprising a β-hydroxyaspartic acid derivative of the following chemical formula (1):

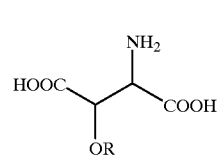
(1)

wherein R represents an aromatic acyl group which may be substituted on the ring, a straight or branched lower aliphatic acyl group, an aryl group which may be substituted on the ring, an aralkyl group which may be substituted on the ring, or a straight or branched lower alkyl group; or a salt thereof.

* * * * *